United States Patent [19]

Herkes

[11] 4,020,051
[45] Apr. 26, 1977

[54] CONTROL OF NITROGEN OXIDE REACTIONS IN OFF-GASES FROM THE DIAZOTIZATION/COUPLING OF AROMATIC AMINES

[75] Inventor: Frank Edward Herkes, Wilmington, Del.

[73] Assignee: E. I. Du Pont de Nemours and Company, Wilmington, Del.

[22] Filed: Nov. 25, 1975

[21] Appl. No.: 635,058

[52] U.S. Cl. .......................... 260/140 R; 260/141; 260/578; 423/235; 423/245; 423/400; 423/405
[51] Int. Cl.$^2$ ............. C07C 115/00; C07C 113/00; C01B 21/00; B01J 8/00
[58] Field of Search ............ 260/140; 423/235, 245

[56] References Cited
UNITED STATES PATENTS

| | | | |
|---|---|---|---|
| 2,133,037 | 10/1938 | Moyer | 360/140 |
| 2,894,942 | 7/1959 | Hydro et al. | 260/205 |

OTHER PUBLICATIONS

Filippuichev et al, Chemical Abstracts, vol. 28, 3720, 7–8 (1934).
Sutcliffe et al, Chemical Abstracts, vol. 69, No. 87957p (1968).
Houben–Weyl, "Methoden der Organischen Chemie", Vol. X/3, p. 712 (1965).
Remy, "Treatise on Inorganic Chemistry", vol. I, pp. 598 and 599 (1956).

Primary Examiner—Floyd D. Higel

[57] ABSTRACT

The deposition of an aromatic diazonium nitrate on the walls of a pipeline through which is conducted a residual gas produced in the diazotization of a primary aromatic monoamine is prevented by heating the walls of the pipeline, limiting the residence time of the gas in the pipeline, or providing for the absence of nitrogen dioxide in the gas. Nitrogen dioxide can form in the pipeline when nitric oxide and molecular oxygen are present, but the deposition of the diazonium nitrate, formed from the nitrogen dioxide via a reaction with the monoamine, is prevented by the hot pipeline walls and/or short residence time.

12 Claims, No Drawings

CONTROL OF NITROGEN OXIDE REACTIONS IN OFF-GASES FROM THE DIAZOTIZATION/COUPLING OF AROMATIC AMINES

BACKGROUND OF THE INVENTION
1. Field of the Invention

The present invention relates to the formation of 1,3-diaryl triazenes, e.g., 1,3-diphenyltriazene, by the diazotization-coupling of primary aromatic monoamines, e.g., aniline.

2. Description of the Prior Art 1,3-Diaryl triazenes (also referred to as diazoamino aryl compounds) can be made to undergo rearrangement by heating, e.g., in the presence of a Friedel-Crafts catalyst, to form aromatic amino azo compounds. The latter are useful for the preparation of aromatic diamines by reduction with hydrogen. The diamines, in turn, are useful as intermediates in the preparation of polymers, antioxidants, etc.

U.S. Pat. No. 2,894,942 describes the formation of aromatic amino azo compounds by adding an inorganic nitrite to a mixture of an excess of a primary aryl monoamine, a mineral acid, and a Friedel-Crafts catalyst while the temperature is 0°–50° C., and thereafter heating up to about 40°–75° C. A portion of the amine is diazotized and the diazonium salt couples with unreacted amine to form the diazoamino aryl compound, which rearranges to the amino azo compound under the combined influence of the catalyst and heat.

A recently discovered process for diazotizing/coupling primary aromatic monoamines involves the reaction of the monoamine with a diluted nitrogen oxide-containing gas mixture derived from the oxidation of ammonia. One of the advantages of this process, as contrasted to the nitrite/acid diazotization method, is that no salt byproducts are formed that require troublesome salt separation and disposal procedures. In the aforesaid diazotization/coupling process, a gas mixture comprising a diluted nitrogen oxide component selected from the group consisting of nitrogen dioxide ($NO_2$) and mixtures of nitrogen dioxide and nitric oxide (the nitrogen oxide component being represented by the formula $NO_x$ wherein $x$ is $(1+n)$, $n$ being the $NO_2$ fraction of the nitrogen oxide component, and generally has a value of 1.1 to 2.0, preferably about from 1.3 to 1.7) is contacted with the monoamine in the liquid phase, the contact between the $NO_x$ gas and the liquid reaction mixture being interrupted while at least about 5 percent, and preferably at least about 40 percent, by weight of the monoamine remains unconsumed. Thereafter, a residual gas consisting chiefly of the diluent, usually nitrogen, present in the oxygen-containing gas used to produce the nitrogen oxide-containing gas mixture from ammonia, and containing possibly unreacted $NO_x$ and oxygen as well as water, monoamine, and 1,3-diaryl triazene in the vapor phase is separated from the triazene-containing reaction liquid. The excess monoamine present in the reaction mixture enables the initially formed diazonium nitrate to couple instantaneously with the monoamine to form the triazene and thereby prevents the build-up of uncoupled diazonium nitrate in the reaction mixture. The accumulation of the nitrate anywhere in the reaction system is undesirable because of the potential explosion hazard created thereby.

SUMMARY OF THE INVENTION

The present invention provides an improved process for preparing a 1,3-diaryl triazene by contacting an excess of a primary aromatic monoamine in the liquid phase with a diazotizing agent therefor, preferably with a nitrogen oxide-containing gas mixture derived from the oxidation of ammonia; and separating a residual gas from the triazene-containing reaction liquid.

The improvement of the invention comprises conducting the residual gas (comprising, in the preferred diazotization/coupling system, a major amount of a diluent such as nitrogen, and small amounts of water, unreacted primary aromatic monoamine, the 1,3-diaryl triazene product, one or more nitrogen oxides, usually nitric oxide, and possibly oxygen) through a pipeline to a waste-gas-disposal system under conditions such that an aromatic diazonium nitrate fails to deposit on the walls of the pipeline by virtue of (a) the temperature of the walls, e.g., a temperature in the range of about from 55° to 125° C; (b) the limited residence time of the gas in the pipeline, dependent on the rates of the reactions which must occur in the gas before the conditions for diazonium salt formation are reached, e.g., the rate of oxidation of nitric oxide to nitrogen dioxide when molecular oxygen is present; or (c) the absence of nitrogen dioxide in the gas.

DETAILED DESCRIPTION

The process of this invention can be employed in conjunction with any procedure wherein a primary aromatic monoamine is diazotized, leaving a residual gas containing unreacted monoamine and one or more nitrogen oxides, e.g., as may occur in the ventilating flues of vats in which amines are diazotized with an inorganic nitrite and a mineral acid (Filippuichev, S.F., et al., Anilinokrasochnaya Prom. 3,351–5, Chemical Abstracts 28, 3720). (The term "residual gas" as used herein denotes the spent gas from a gas/liquid reaction system as well as the vapor produced by the volatilization of a reaction liquid.) However as was explained above,, the preferred diazotization/coupling process is carried out by contacting the monoamine with a nitrogen oxide-containing gas mixture derived from the oxidation of ammonia. In the latter process, the gas mixture used for the diazotization/coupling is made by passing ammonia gas and a gas comprising diluted molecular oxygen, preferably air, over a catalyst at elevated temperature whereby the ammonia is oxidized to nitric oxide (NO); and cooling the resulting gas, comprising a mixture of nitric oxide, oxygen, water vapor, and diluent, e.g., nitrogen, whereby the nitric oxide is oxidized, either completely but preferably only in part, to nitrogen dioxide ($NO_2$ resulting in a gas mixture comprising nitrogen dioxide ($NO_2$), preferably also nitric oxide, the diluent, water vapor, and, depending on the specific conditions used, possibly some residual oxygen. The nitrogen oxide component of the gas mixture, i.e., $NO_2$ or $NO_2/NO$, is represented by the aforementioned formula $NO_x$ wherein $x$ is $(1+n)$ and generally has a value of from about 1.1 to 2 ($n$ is the $NO_2$ fraction of the nitrogen oxide component). Under the usual circumstances, the $NO_x$ concentration of the gas mixture produced is about 10–12 mole percent, but it can be adjusted as will be described hereinafter to span the range of about from 1 to 20 mole percent, and even up to about 30 mole percent, and such concentrations can be used for the diazotization/coupling reaction.

The oxidation of ammonia, and subsequently of the resulting nitric oxide, by air at elevated temperature to produce gas mixtures containing $NO_x$ as defined above has been amply described in the literature. For the oxidation to nitric oxide, usually a platinum or platinum alloy catalyst is used, together with temperatures in the range of about from 800° to 950° C. Pressures of about from atmospheric to 120 psiga (8.16 atmospheres) have been used. Oxygen-enriched air also can be used. The ammonia content of the ammonia/air mixture generally ranges about from 11 to 13 mole percent, and the oxygen/ammonia mole ratio about from 1.3/1 to 1.7/1. Further details can be learned by reference to > Mellor's Comprehensive Treatise on Inorganic and Theoretical Chemistry, Vol. VIII, Suppl. II, Sec. XXIX; or Riegel's *Handbook of Industrial Chemistry*, Ed. 7, Van Nostrand, 1974, pp. 94–98, the disclosures of which are incorporated herein by reference.

In contrast to the oxidation of ammonia, the oxidation of nitric oxide occurs at a less elevated temperature, e.g., in the range of about from 100° to 500° C, the rate of oxidation being higher at lower temperatures and higher pressures. The value of $x$ in the $NO_x$ component of the resulting gas mixture, which is a measure of the state of oxidation of the nitrogen oxide component, can be varied by suitable selection of the pressure, temperature, and contact time of the gases in the NO oxidizer, the $NO_2$ fraction of the $NO_x$ produced increasing with the contact time. The contact time required to produce a desired $NO_2$ fraction can be determined from known rates of oxidation at various temperatures and pressures.

The $NO_x$ component of the gas mixture to be contacted with the monoamine in the preferred diazotization/coupling system can be $NO_2$ alone, but preferably is a combination of $NO_2$ and NO. When $NO_x$ is $NO_2$ alone, i.e., when $x$ is 2, the yield of 1,3-diaryl triazene is apt to be lower owing to (1) a competing nitration reaction, which results, for example, in the formation of p- and o- nitroanilines when the reactant is aniline, and (2) rearrangement of the triazene to the amino azo compound catalyzed by nitric acid produced as a by-product. Although the nitro and amino azo products are also useful in that they can be reduced to diamines, it is preferred that as much of the monoamine as possible be converted to the triazene in the diazotization/coupling step, and for this reason an $NO_x$ wherein $x$ is less than 2 is preferred. Minimizing the formation of the amino azo compounds during the diazotization/coupling decreases the likelihood of the formation of by-products which could subsequently prove troublesome.

The value of $x$ in $NO_x$ in the gas mixture used for the preferred diazotization system will be at least about 1.1 and preferably at least about 1.3. As the $NO_2$ fraction of the mixture decreases, more of the nitric oxide is unutilized and conversion to the triazene consequently is low. At very low $NO_2$ fractions, excessive quantities of unutilized nitric oxide would have to be handled. Preferably $x$ has a value no greater than about 1.7 so as to avoid the increased chance that rearrangement, nitration, and/or oxidation reactions will occur, which reactions could subsequently prove troublesome, as mentioned previously. On the basis of good utilization of the nitric oxide as well as the minimizing of side-reactions, an $NO_x$ wherein $x$ is close to a value of about 1.5 (50/50 $NO_2$/NO mixtures), e.g., about 1.4 to 1.6, is especially preferred.

The $NO_x$-containing gas mixture is contacted with an excess of monoamine so that the initially formed diazonium salt (nitrite or nitrate) can couple instantaneously with unreacted monoamine to form a 1.3-diaryl triazene. "Excess" monoamine means that unconsumed or unreacted monoamine is present in the reaction mixture at all times, with at least about 5 percent, and preferably at least about 40 percent, of the monoamine remaining unconverted to products. If the contact between the $NO_x$ and the reaction mixture is interrupted while at least about 5 percent of the monoamine remains unconsumed, the build-up of uncoupled diazonium salts in the reaction mixture can be avoided.

In the preferred diazotization/coupling system, the monoamine is reacted in the liquid phase. A solvent or diluent is not required with monoamines which are liquid under the reaction conditions, and for economic reasons these preferably are employed in the neat condition. If the monoamine is a solid under the reaction conditions, a solvent therefor can be used, e.g., an aromatic hydrocarbon such as benzene or xylene, or a halogenated aliphatic hydrocarbon such as carbon tetrachloride or methylene chloride. The presence of a solvent or a diluent liquid such as water with a liquid monoamine has no adverse effect on the reaction.

There should be sufficient liquid in the reaction mixture to form a stirrable slurry or slush, or a solution, with the solid triazene formed. Otherwise, even if excess monoamine is present, the diffusion of the gas through the reaction mixture may be so slow that the diazonium nitrate can accumulate on the surface of the solid triazene as a result of a reaction between the gas and the triazene. For this reason, when the amount of unconsumed monoamine is at a level as low as 5%, another solvent is employed to maintain stirrability. With larger amounts of unconsumed monoamine present, the required mobility of the reaction mixture may be achieved with neat monoamine by employing higher reaction temperatures. Preferably, the reaction product is a homogeneous liquid and for this reason, when neat monoamine is used, the amount thereof remaining unconsumed is sufficient to act as a solvent for the triazene.

In any case, whether neat, dissolved, or diluted monoamine is used, the contact between the $NO_x$ gas and the reaction mixture preferably is broken while at least about 40 percent, and most preferably at least about 60 percent, by weight of the monoamine remains unconsumed. The yield of triazene drops off sharply owing to rearrangement when the unconsumed monoamine falls below about 40 percent, and the yield drop may even become significant when the unconsumed monoamine falls below about 60 percent. Preferably, the unconsumed monoamine will not exceed about 85 percent to avoid the handling and work-up of excessively large volumes of materials containing low concentrations of the triazene. In a semi-batch-type operation, the $NO_x$ gas is added to the monoamine, and the addition stopped when the selected monoamine consumption has been reached, as can be determined by analysis of the reaction mixture. In a continuous operation the product stream is separated from the gas stream when the selected monoamine consumption has been reached, as can be determined by analysis of the product stream.

The residual gas separated from the triazene-containing reaction liquid consists chiefly of the diluent present in the molecular-oxygen-containing gas used to produce the nitrogen oxide-containing gas mixture from ammonia. Since the oxygen-containing gas usually is air, the residual gas from the diazotization/coupling reaction usually is chiefly nitrogen and additionally contains small quantities of water, the monoamine, the 1,3-diaryl triazene, unreacted $NO_x$, and possibly oxygen. The amount of water, monoamine, and triazene in the residual gas depends on the temperature and pressure in the reaction vessel. When the $NO_x$ contacted with the monoamine is a mixture of nitric oxide and nitrogen dioxide, unreacted $NO_x$ in the residual gas is usually only NO. Unreacted $NO_2$ may appear in the residual gas when the starting $NO_x$ in $NO_2$ and the degree of gas/liquid contact in the reaction vessel is not adequate for complete reaction of the $NO_2$. The nitric oxide concentration in the residual gas depends on the state of oxidation of the initial gas mixture, i.e., on the value of $x$ in the $NO_x$ contacted with the monoamine, higher NO concentrations in the residual gas being encountered with lower values of $x$. The NO concentration in the residual gas has been found to vary from 0.07 to 3.2 percent by volume over the range of $x$ values of the starting $NO_x$ from 1.3 to 2.0, a concentration of 0.44 percent by volume being encountered when the value of $x$ in the starting $NO_x$ is 1.65.

I have found that, contrary to prior teachings (e.g., Drago, R.S., et al., J. Am. Chem. Soc. 83, 1819–1822 (1961)), primary aromatic monoamines do not react with nitric oxide, and that the formation of a diazonium salt in the residual gas does not occur unless nitrogen dioxide is present therein. Although, as explained above, nitrogen dioxide usually will not be present in the residual gas as it is separated from the reaction liquid, the dioxide can form if molecular oxygen and nitric oxide are present. Therefore, in one embodiment of the present process, molecular oxygen is excluded from the residual gas by employing a substantially oxygen-free $NO_x$-containing gas mixture for the diazotization/coupling reaction, i.e., a gas mixture containing less than about 500 parts per million of oxygen. In this way, the rate at which the nitric oxide in the residual gas can be oxidized to nitrogen dioxide is minimized owing to the low concentration of oxygen therein. To achieve the substantial absence of oxygen in the gas mixture to be used in the diazotization/coupling reaction, the ammonia concentration of the ammonia/oxygen-containing gas mixture in the ammonia oxidation step of the process preferably is as high as possible within the safe operating range, e.g., about from 11 to 13 mole percent ammonia. Also, in the nitric oxide oxidation, the contact time is sufficient to permit full consumption of the oxygen, and the temperature of the gas mixture produced does not exceed about 275° C at atmospheric pressure, thereby minimizing the chances that the reverse reaction, i.e., nitrogen dioxide decomposing into nitric oxide and oxygen, will occur.

In other embodiments of the present process, molecular oxygen is present in the residual gas, and diazonium nitrate deposition on the walls of the pipeline through which the gas is conducted to a treatment system is prevented either by (a) limiting the residence time of the gas in the pipeline so that the gas has gone into the disposal system (e.g., wherein the amine is separated out of the gas, or wherein the gas is exposed to high abatement temperatures) before the diazonium nitrate can form; or (b) maintaining the walls of the pipeline at a temperature at which the rate of diazonium nitrate decomposition is at least as high as the rate of diazonium nitrate formation, e.g., above about 50° C in the case of benzenediazonium nitrate.

The time that will elapse before the diazonium nitrate begins to form depends on the components of the gas and their concentrations, and on the rates of the reactions which must occur in the gas before the conditions for diazonium nitrate formation are reached. Diazonium nitrate will form soonest in the rare circumstance in which nitrogen dioxide is present in the residual gas as the gas is separated from the reaction liquid. This is because the nitrogen dioxide, alone or with nitric oxide which usually is present, reacts rapidly with the monoamine to form the 1,3-diaryl triazene if the monoamine is in excess, or the diazonium nitrate if the nitrogen oxide(s) are in excess. Since the monoamine is rapidly consumed so as to result in an excess of the nitrogen oxide(s), the diazonium nitrate rapidly becomes the product of the monoamine/nitrogen oxide reaction. In such a situation, the diazonium nitrate may deposit on the walls of the pipeline instantaneously, thereby necessitating measures to decompose the salt as it is formed to prevent its accumulation. Therefore, when the residual gas as it is separated from the reaction liquid contains nitrogen dioxide, the wall of the pipeline are maintained at a temperature above the decomposition temperature of the diazonium nitrate (above the 50° C for benzenediazonium nitrate), e.g., a temperature in the range of about from 55° to 125° C.

If the residual gas as it is separated from the reaction liquid contains molecular oxygen, but no nitrogen dioxide, and therefore the presence of nitrogen dioxide in the gas in the pipeline results from the reaction of nitric oxide and oxygen in the gas, diazonium nitrate accumulation can be prevented by controlling the residence time of the gas in the pipeline. The reaction of nitric oxide and oxygen is slow relative to the reaction of the amine to form the diazonium salt or the triazene, and diazonium nitrate deposition may not occur for several seconds, the exact time depending on the conditions prevailing in the pipeline. For example, when a residual gas at a temperature of 50° C and a pressure of one atmosphere and containing (by volume) 1% nitric oxide, 3% oxygen, and 0.5% aniline passes through an off-gas line having a 25° to 35° C wall temperature, the deposition of benzenediazonium nitrate on the walls occurs in about 5 seconds. Therefore, in this case the present process can be carried out by limiting the residence time of the gas in the pipeline to about 4 seconds or less. The higher the pressure of the gas, or the higher the nitric oxide or oxygen concentration, the lower the residence time required to prevent diazonium nitrate deposition. For example, under the just-described conditions, as the nitric oxide concentration is increased to 1.5%, the maximum residence time should be lowered to 2 seconds.

It has been found that aromatic diazonium nitrates can be made to undergo smooth thermal decomposition as fast as they form in the off-gas line if the walls of the pipeline are heated to a temperature above the decomposition temperature of the nitrate. Therefore, in the present process, when oxygen is present in the residual gas and the residence time of the gas in the pipeline is long enough for the diazonium nitrate to form, the walls of the pipeline are maintained above the decomposition temperature of the nitrate. The minimum wall temperature that will be used will be one which will assure the instantaneous decomposition of the particular diazonium salt that can form, i.e., about 55° C for benzenediazonium nitrate. The maximum temperature will depend mainly on the thermal behavior of other materials in the off-gas, e.g., the triazene, and on economic considerations. Based on these factors, the wall temperature generally will be in the range of about from 55° to 125° C, a range of about from 55° to 75° C being preferred in the case in which benzenediazonium nitrate is involved.

In a preferred embodiment of this process, when oxygen is present in the residual gas, the walls of the pipeline are heated as described and the residence time of the gas in the pipeline is limited as described. This provides a redundancy factor in the means taken to avoid diazonium nitrate accumulation in the pipeline, a potentially hazardous condition as was mentioned previously. Of course, one or both of these measures can be adopted even when the residual gas contains less than 500 parts per million of oxygen, especially at higher pressures and NO concentrations in the residual gas and oxygen concentrations close to the 500 parts per million point. With an oxygen concentration of about 200 parts per million, more than 17 seconds may elapse before diazonium nitrate deposition occurs, when the NO concentration is 2% and the pressure is 5 psiga (0.3 atmosphere). In such a case, measures to limit the residence time to a level below that normally prevailing in off-gas trains usually will be unnecessary. However, under other combinations of gas concentrations and pressure, control of residence time and/or wall temperature may be used.

With respect to other reaction conditions to be employed in the diazotization/coupling process wherein the diazotization is effected by a nitrogen oxide-containing gas mixture derived from the oxidation of ammonia, the $NO_x$ concentration of the gas mixture produced by the air oxidation of nitric oxide usually is about 10–12 mole percent, and depends on the oxygen/ammonia mole ratio and the yield, higher oxygen/ammonia ratios and yields being associated with higher $NO_x$ concentrations. In theory, up to about 17% $NO_x$ is attainable. A range of about from 1 to 20 mole percent $NO_x$ can be achieved by dilution or water vapor removal, for example, and mixtures having such concentrations can be used in the diazotization/coupling reaction. Mixtures having a higher $NO_x$ concentration, e.g., up to about 30 mole percent, are attainable by combining the 1 to 20 percent mixtures with more highly concentrated mixtures, and also can be used in the diazotization/coupling reaction. However, concentrations above about 12 mole percent are not preferred owing to the added expense of achieving such concentrations and the loss of the beneficial effects of dilution with respect to reaction control. In the diazotization/coupling, there appears to be no benefit resulting from diluting, or removing water vapor from, the mixture produced by the nitric oxide oxidation, and accordingly the 10 to 12 mole percent $NO_x$ concentration is especially preferred.

In a preferred diazotization/coupling process the temperature of the $NO_x$-containing gas mixture just prior to its contact with the monoamine preferably is in the range of about from 25° to 350° C, and more preferably from 110° to 275° C. When, as in the usual case, water vapor is present in the mixture, a gas temperature of at least about 110° C prevents the condensation of water vapor from the gas with the attendant formation of nitric acid, which catalyzes the rearrangement of the 1,3-diaryl triazene to the amino azo compound. Above about 350° C, oxidative degradation of the monoamine occurs, and furthermore it becomes more difficult to maintain higher states of oxidation of the $NO_x$ at such temperatures, owing to the increased rate of decomposition of nitrogen dioxide into nitric oxide and oxygen. Temperatures above about 275° C are not preferred when oxygen is to be excluded, and also because strenuous cooling measures are required to maintain the amine in the required temperature range, as will be described late.

The diazotization/coupling temperature, or the temperature at which the monoamine is maintained while it is in contact with the $NO_x$-containing gas mixture, is in the range of about from 25° to 90° C, and preferably 40° to 60° C. Temperatures above about 90° C will not be employed owing to the instability of the triazene and consequent yield losses. The specific temperature employed will depend on various factors. First, the temperature of the amine rises when it is contacted with the hot $NO_x$ gas mixture as a result of the heat of reaction as well as of the heat transferred to the amine from the hot gas. Consequently, it will be convenient to employ a reaction temperature in the vicinity of the temperature which results from these exothermic and transfer conditions and which can be maintained easily by modest cooling techniques, e.g., water cooling.

The diazotization/coupling reaction temperature used may be selected also on the basis of the solubility of the triazene and the amount of amine consumed. If a homogeneous product is desired, it may be desirable to employ a temperature at which the triazene is soluble in the amine at the operating consumption level. For example, 1,3-diphenyltriazene is sufficiently soluble in aniline at 50° to 55° C that at such temperature the product is homogeneous when about 20 to 40% of the aniline has been consumed. At consumption levels above 40%, higher temperatures are required for homogeneity. Therefore, in the diazotization/coupling of aniline, a temperature of about 50° to 55° C is especially preferred at consumption levels up to about 40%, and higher temperatures at higher consumption levels, e.g., up to about 90° C at consumption levels above about 40%.

Temperatures as low as about 25° C can be employed in the diazotization/coupling reaction, homogeneity in the case of aniline still being attainable at this temperature at a 20% consumption level. The range of about from 40° to 60° C is preferred on the basis of all factors considered, i.e., yield, ease of maintaining temperature, homogeneity of product, etc.

The preferred diazotizationcoupling process operates satisfactorily at atmospheric pressures although elevated pressures, usually those employed in the nitric oxide oxidation, e.g., up to about 120 psiga (8.16 atmospheres), can be used.

Agitation of the reaction mixture has no notable effect on the course of the reaction per se, but helps to disperse the gas in the monoamine and promote good contact between gas and liquid phases.

The present process is applicable to the diazotization/coupling of unsubstituted primary carbocyclic aromatic monoamines, e.g., aniline and $\alpha$ - and $\beta$-naphthylamine, as well as of primary carbocyclic aromatic monoamines having substituents which are inert to $NO_x$, e.g., alkyl, halo, haloalkyl, alkoxy, and nitro substituents. Preferred alkyl, haloalkyl, and alkoxy substituents have 1 to 4 carbon atoms. Suitable substituted monoamines include, for example, o- and m-toluidines; 2,3-, 2,5-, 2,6-, and 3,5-dimethylanilines, trifluoromethylaniline; and o- and m-chloro-, bromo-, fluoro-, and nitroanilines.

The invention is illustrated by the following examples

EXAMPLE 1

A gas mixture having the composition (molar) 4.5% NO, 6.8% $NO_2$, 68.8% nitrogen, and 19.9% water vapor (11.3% $NO_x$ concentration; $x = 1.6$) is obtained when an ammonia/air mixture containing 12.1 mole percent ammonia, 18.1 mole percent oxygen, and 1.7 mole percent water vapor (from ambient air) is passed over a platinum-rhodium alloy (10% rhodium) guaze catalyst heated to 900° C at a pressure of 120 psi (8.16 atmospheres), and the resulting gas mixture is cooled to a temperature of 200° C and held at about the same pressure.

Aniline (132.4 grams) at room temperature is charged to a 150-milliliter glass reactor equipped with an agitator, an outer condenser sleeve, a heated side-arm capillary gas inlet tube (near the bottom of the reactor), a thermocouple, and a 150-millimeter-long upper exit tube connected to a 150-millimeter long water-cooled condenser.

The above-described gas mixture, at an average temperature of 200° C (175 to 225° C) and a pressure of one atmosphere, is fed into the room-temperature aniline via the heated gas inlet tube at a rate of 342 milliliters per minute. During the addition of the gas, the aniline is agitated at about 2000 revolutions per minute. The bulk temperature of the aniline rises to 45° to 50° C and is maintained there by air cooling. Off-gases (containing 0.5-0.7 vol. % NO, no $NO_2$, and no oxygen) leave the reactor through the exit tube and condenser at a rate of 274 milliliters per minute. The hold-up time in the exit tube and condenser maintained at 25° C is about 11 seconds. No benzenediazonium nitrate deposition is observed in the off-gas line.

The gas flow is stopped after 180 minutes, whereupon the reaction mixture is allowed to cool to 30° C, and the organic layer separated from the aqueous layer. The composition of the organic layer (133.2 gram), after neutralization, by weight is as follows: 19.8% 1,3-diphenyltriazene, 1.63% p-aminoazobenzene, 0.121% o-amino-azobenzene, 0.177% o-, m-, and p-aminodiphenyls, 0.086% $HNO_3$, 1.9% $H_2O$, and 73.1% aniline. Based on total accountable organic products, 21.7% of the aniline has been converted to products after 180 minutes. On this basis, the yield of 1,3-diphenyltriazene is 91.1% (weight of triazene divided by the weight of total accountable solids derived from aniline).

EXAMPLE 2

The procedure described in Example 1 is repeated with the exception that a 300-milliliter reactor is employed and the gas mixture used has the composition (molar) 10% $NO_2$ and 90% nitrogen. This mixture is obtained when the ammonia molar concentration is 10.7% and oxygen 18.1%, and water vapor is subsequently removed from the product gas. In this case, the gas mixture, at a temperature of 25° C, is fed into the aniline (199.5 grams) at a rate of 375 milliliters per minute, the bulk temperature of the aniline rising to 35° C. Gas flow is stopped after 204 minutes. The weight of organic layer is 206.7 grams. Based on an aniline conversion of 16.4%, the yield of 1,3-diphenyltriazene is 42.4%, p-aminoazobenzene 31.6%, p-nitroaniline 16.3%, and o-nitroaniline 9.9%. The off-gas (nitrogen, 700 parts per million $NO_2$, aniline, water vapor, no oxygen) is chilled to 10° C in the condenser to condense out aniline and triazene vapors and is vented. The hold-up time in the off-gas train maintained at about 15° C is 8.5 seconds. No diazonium nitrate deposition is observed.

EXAMPLE 3

Aniline (69.9 grams) at room temperature is charged to a 150-milliliter glass reactor equipped with an outer condenser sleeve, two heated side-arm capillary gas inlet tubes (near the bottom of the reactor), a thermocouple, and a 150 millimeter-long water-cooled condenser.

A gas mixture having the composition 5.4% $NO_2$, 2.9% NO, 17% water vapor and 74.7% nitrogen at an average temperature of 200° C (175° to 225° C) and a pressure of 1 atmosphere is fed into the room temperature aniline via one of the heated gas inlet tubes at a rate of 150 milliliters per minute. A second gas mixture having the composition of 3% oxygen and 97% nitrogen at an average temperature of 200° C and a pressure of 1 atmosphere is fed into the aniline via a second heated gas inlet tube at a rate of 125 milliliters per minute such as to produce a final composition of 2.9% $NO_2$, 1.6% NO, 9.1% water vapor, 1.4% $O_2$ and 85% nitrogen. This mixture simulates a gas which has been produced by the oxidation of ammonia according to the described process followed by dilution with nitrogen to give a concentration of 4.5% $NO_x$. During the addition of the gases, the aniline is stirred at about 1000 revolutions per minute. The bulk temperature rises to 45° to 50° C and is maintained there by air cooling.

The gas flow is stopped after 211 minutes. The weight of organic layer is 68.2 grams. Based on an aniline conversion of 24.8%, the yield of 1,3-diphenyltriazene is 76.6%, p-aminoazobenzene 19.3%, o-aminoazobenzene 1.65, p-nitroaniline 1.5%, and o-nitroaniline 1.0%.

The off-gas contains 0.5 volume percent NO and 1.4 volume percent oxygen. No benzenediazonium nitrate deposits on the 25° walls of the off-gas line in the approximately 9 seconds the gas is held up therein.

EXAMPLE 4

A portion of the nitrous gas stream from a commercial ammonia oxidation process (AOP) unit engaged in the production of nitric acid is continuously withdrawn and reacted with aniline for a period of 155 minutes. In the AOP unit an ammonia-air mixture routinely containing 11.4 to 11.6 mole percent ammonia by analysis is catalytically burned over a platinum guaze catalyst at about 900° C and 125 psig (8.5 atmospheres) to produce a nitrous gas containing nitric oxide, water vapor, some unreacted oxygen (3% by vol.), and the rest nitrogen. At a point in the AOP unit where the gas has been cooled to about 540° C, a portion of the gas is tapped off by pipeline at a rate of 140 pounds (63.6 kilograms) per hour, through a heat exchanger where it is cooled to 190° C in about 1.5 seconds before being fed to a reactor tube where it is contacted with recirculating aniline solution at a flow rate of 25 gallons (95 liters) per minute. The exit of the reactor tube is in a gas/liquid separator designed for continuous drawoff. The reaction product solution (1,3-diphenyltriazene dissolved in aniline) and gases produced in the reactor pass into the separator, liquid being withdrawn from the separator continuously. Fresh aniline is continuously fed into the liquid stream emanating from the separator, at a rate of 480 pounds (216 kilograms) per hour, and the product solution is continuously withdrawn to maintain constant inventory in the reactor and separator. Part of the withdrawn liquid is recovered, and part of it is recirculated through a cooler (to remove heat of reaction from the system and maintain a temperature of 50° to 55° C in the reactor and separator) and then to the reactor. The temperature at the reactor tube inlet is 77° to 50° C; the pressure at the reactor inlet is 35 psig (2.4 atmospheres) and at the exit (in the gas/liquid separator) 4 psig (0.3 atmosphere). The volume of the reaction tube is 0.186 cubic feet (52 liters). A liquid holdup of about 3 gallons (11 liters) is maintained in the separator whose total volume is about 12 gallons (45 liters).

Analyses of samples of the product solution are given in the following table. The yield of 1,3-diphenyltriazene, based on aniline, is 89 percent (17% aniline conversion).

|  | wt. % |
|---|---|
| 1,3-Diphenyltriazene | 16.3 |
| p-Aminoazobenzene | 1.77 |
| o-Aminoazobenzene | 0.16 |
| Aminodiphenyls | 0.07 |

Off-gas (50° to 55° C) leaving the separator comprises nitrogen, 0.4 volume percent NO, 3 volume percent oxygen, water, and aniline vapor (no $NO_2$). This gas is passed through a 60° C wall off-gas line at 4 psiga (0.3 atmosphere) with a residence time of 0.05 to 0.1 second before entering a water scrubber to remove aniline. No benzenediazonium nitrate deposition is observed.

CONTROL EXPERIMENT

If the preceding off-gas contains 1% NO, the wall temperature is 25° C, and the pressure 1 atmosphere, benzenediazonium nitrate deposition occurs in 5 seconds. If, in addition, the temperature of the off-gas leaving the separator is 25° C, benzenediazonium nitrate deposits on the wall of the off-gas line also in 5 seconds.

I claim:

1. In a process for preparing a 1,3-diaryl triazene by the diazotization and coupling of a primary carboxyclic aromatic monoamine in the liquid phase whereby a residual gas containing one or more nitrogen oxides and unreacted primary carbocyclic aromatic monoamine is separated from the triazene-containing reaction liquid, the improvement comprising conducting said residual gas through a pipeline to a waste-gas disposal system and performing at least one of the following steps: heating the walls of said pipeline during the passage of said residual gas therethrough conducting said residual gas out of said pipeline before a carbocyclic aromatic diazonium nitrate deposits on the walls thereof, and preventing the substantial entry of formation of nitrogen dioxide in said pipeline.

2. A process of claim 1 wherein said residual gas as it is separated from said reaction liquid and enters said pipeline contains nitrogen dioxide and the walls of said pipeline are maintained at a temperature in the range of about from 55° to 125° C.

3. A process of claim 1 wherein said residual gas as it is separated from said reaction liquid and enters said pipeline contains nitric oxide, substantially no nitrogen dioxide, and is essentially free of molecular oxygen, whereby the substantial formation of nitrogen dioxide in said pipeline is prevented.

4. A process of claim 1 wherein said residual gas as it is separated from said reaction liquid and enters said pipeline contains nitric oxide, molecular oxygen, and substantially no nitrogen dioxide, and the walls of said pipeline are maintained at a temperature in the range of about from 55° to 125° C.

5. A process of claim 1 wherein said residual gas as it is separated from said reaction liquid and enters said pipeline contains nitric oxide, molecular oxygen, and substantially no nitrogen dioxide, said gas and is conducted out of said pipeline in up to about 4 seconds.

6. A process of claim 4 wherein said primary carbocyclic aromatic monoamine is aniline and said temperature is in the range of about from 55° to 75° C.

7. A process of claim 3 wherein said 1,3-diaryl triazene is prepared by contacting said monoamine with a substantially oxygen-free gas mixture obtained by catalytically oxidizing ammonia with a gas comprising diluted molecular oxygen, said gas mixture comprising a diluted mixture of nitrogen dioxide and nitric oxide.

8. In a process for preparing a 1,3-diaryl triazene by contacting an excess of a primary carbocyclic aromatic manoamine in the liquid phase with a gas mixture obtained by catalytically oxidizing ammonia with a gas comprising diluted molecular oxygen, said gas mixture comprising a dilute nitrogen oxide component selected from the group consisting of nitrogen dioxide and mixtures of nitrogen dioxide and nitric oxide, and separating from the traizene-containing reaction liquid a residual gas containing one or more nitrogen oxides and unreacted primary carbocyclic aromatic monoamine, the improvement comprising conducting said residual gas to a waste-gas-disposal system through a pipeline whose walls are maintained at a temperature in the range of about from 55° to 125° C.

9. A process of claim 8 wherein said gas is conducted out of said pipeline in up to about 4 seconds.

10. A process of claim 8 wherein said residual gas as it is separated from said reaction liquid and enters said pipeline contains nitric oxide, molecular oxygen, and substantially no nitrogen dioxide.

11. A process of claim 1 wherein said 1,3-diaryl triazene is prepared by contacting said monoamine with a gas mixture obtained by catalytically oxidizing ammonia with a gas comprising diluted molecular oxygen, said gas mixture comprising a dilute mixture of nitrogen dioxide and nitric oxide.

12. A process of claim 11 wherein said residual gas as it is separated from said reaction liquid and enters said pipeline contains nitric oxide, molecular oxygen, and substantially no nitrogen dioxide, and said gas is conducted out of said pipeline in up to about 4 seconds.

* * * * *

UNITED STATES PATENT OFFICE
CERTIFICATE OF CORRECTION

PATENT NO. : 4,020,051
DATED : April 26, 1977
INVENTOR(S) : FRAND EDWARD HERKES

It is certified that error appears in the above-identified patent and that said Letters Patent are hereby corrected as shown below:

Claim 1, line 11: insert a comma after "therethrough";

line 14: change "of" to -- or --.

Claim 5, line 4: "said gas and" should be -- and said gas --.

Signed and Sealed this twenty-sixth Day of July 1977

[SEAL]

Attest:

RUTH C. MASON
Attesting Officer

C. MARSHALL DANN
Commissioner of Patents and Trademarks